United States Patent [19]

Nowicky

[11] Patent Number: 4,970,212
[45] Date of Patent: Nov. 13, 1990

[54] METHOD OF TREATING HUMAN ILLNESSES WHICH COMPROMISE THE ABILITY TO MOUNT AN EFFECTIVE IMMUNOLOGICAL RESPONSE

[76] Inventor: Wassyl Nowicky, Laimgrubengasse 19/5, Vienna, Austria

[21] Appl. No.: 173,564

[22] Filed: Mar. 25, 1988

Related U.S. Application Data

[63] Continuation-in-part of Ser. No. 831,082, Feb. 20, 1986, Pat. No. 4,816,462, which is a continuation of Ser. No. 379,415, May 18, 1982, abandoned.

[51] Int. Cl.$^5$ .................... A61K 31/44; A61K 31/34
[52] U.S. Cl. .................................. 514/279; 514/282; 514/284; 514/468; 514/885; 514/934
[58] Field of Search ............... 514/279, 282, 284, 468, 514/934, 885

[56] References Cited

U.S. PATENT DOCUMENTS 4,259,443  6/1980  Jovanovics et al. ............. 260/244.4

OTHER PUBLICATIONS

Chem. Abst., 69:10383r, 1968.
Chem. Abst., 88:14677x, 1978.
Chem. Abst., 87:78524q, 1977.
Chem. Abst., 84:54026r, 1976.
Chem. Abst., 74:86207k, 1971.

Primary Examiner—John W. Rollins
Attorney, Agent, or Firm—Lyon & Lyon

[57] ABSTRACT

A method is disclosed for treating human patients suffering from illnesses, including AIDS, which compromise their ability to mount an effective immunological response. This method comprises administering to the patient a pharmaceutically acceptable cytostatic alkaloid compound which can be an alkaloid, an alkaloid-phosphate derivative, an alkaloid-thiophosphate derivative, a nitrogen- or phosphorus-containing cytostatic and carcinostatic compound coupled with an alkaloid, an alkaloidphosphate or an alkaloid-thiophosphate derivative, or a salt of such alkaloid compounds, e.g., a thiophosphoric acid triaziridide (Thio-TEPA) derivative of alkaloid extracts of *Chelidonium majus L.* (greater celandine) in the form of the hydrochloride salt, in a pharmaceutically effective amount to reverse T-helper cell deficiency and diminish the overgrowth of T-suppressor cells in the patient.

12 Claims, 15 Drawing Sheets

CHELILUTIN + THIOPHOSPHORIC ACID TRIAZIRIDIDE

COPTISIN + THIOPHOSPHORIC ACID TRIAZIRIDIDE

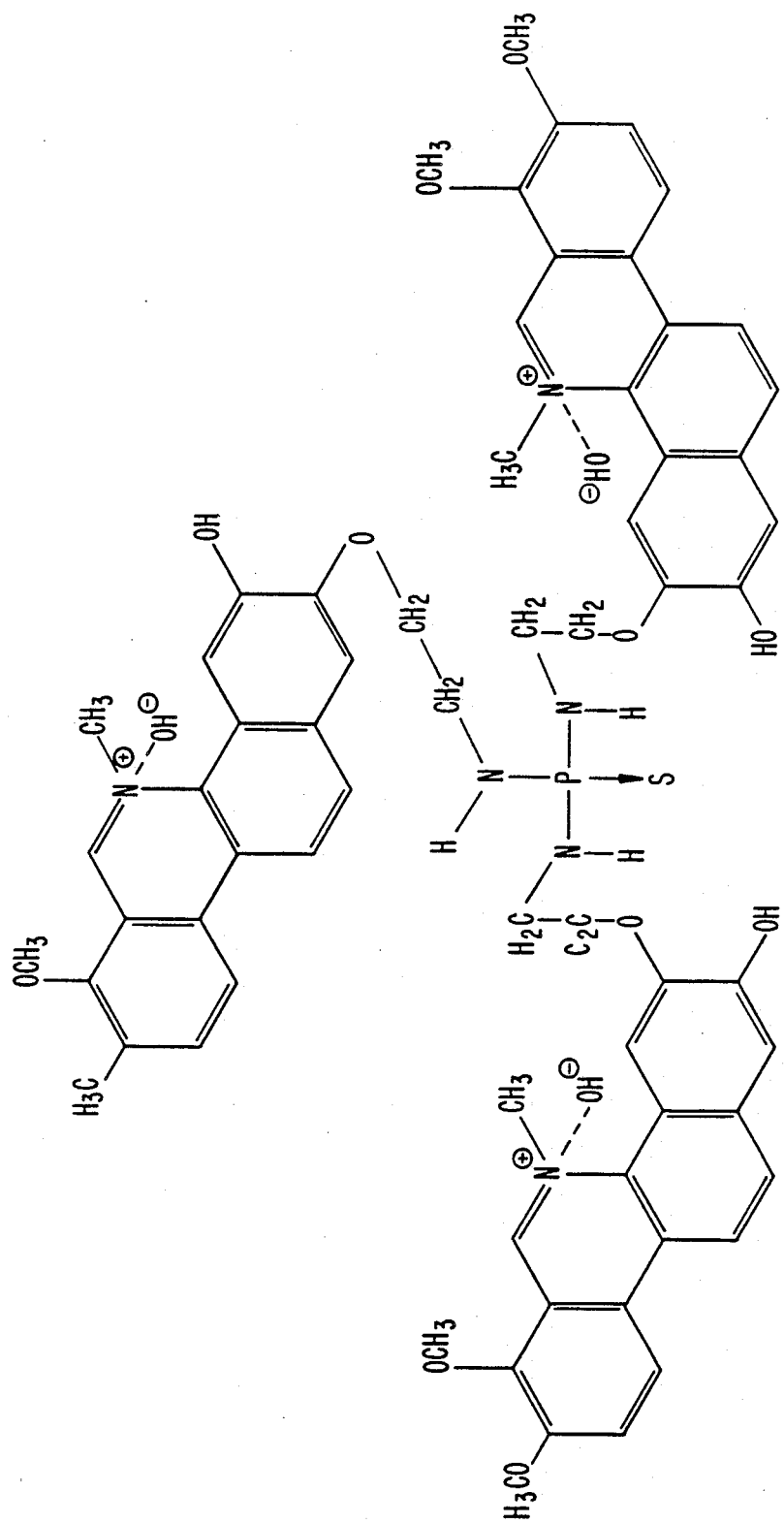
FIG. 2. CHELERYTHRIN + THIOPHOSPHORIC ACID TRIAZIRIDIDE

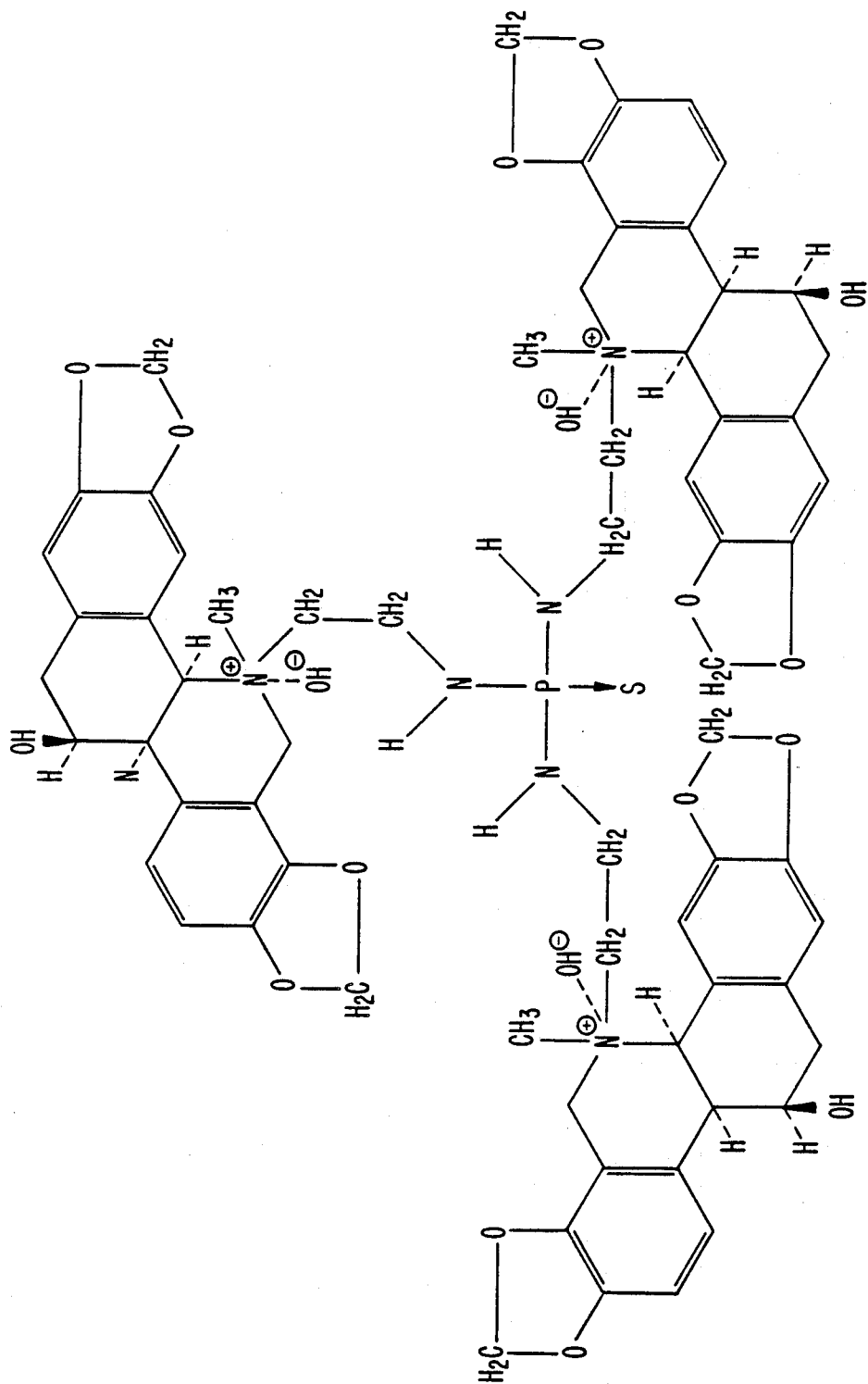
FIG. 4. CHELIDONIN + THIOPHOSPHORIC ACID TRIAZIRIDIDE

PROTOPINE + THIOPHOSPHORIC ACID TRIAZIRIDIDE

METHOD OF TREATING HUMAN ILLNESSES WHICH COMPROMISE THE ABILITY TO MOUNT AN EFFECTIVE IMMUNOLOGICAL RESPONSE

This application is a continuation-in-part of my copending U.S. Pat. application Ser. No. 831,082, filed Feb. 20, 1986, now U.S. Pat. No. 4,816,462, issued Mar. 28, 1989, which in turn is a continuation of abandoned U.S. Pat. application Ser. No. 379,415, filed May 18, 1982.

FIELD OF THE INVENTION

This invention relates to a method of treating human patients suffering from illnesses which compromise their ability to mount an effective immunological response, including the recently-discovered lymphocyte disease Acquired Immune Deficiency Syndrome or AIDS. Such illnesses may be the illness resulting from an original infectious agent or agents, e.g., the so-called Human Immunodeficiency Virus ("HIV"), or ones resulting from introduced opportunistic infectious agents to which an adequate immunological response cannot be mounted by reason of the effects of the original infectious agent or agents on the patient's immune system.

BACKGROUND OF THE INVENTION

AIDS appears to be a disease which may be due to a viral agent, similar to or the same as the viral agents discussed in my aforementioned copending U.S. Pat. application, which causes specific changes in lymphocyte function. Lymphocytes are known to exist in several different forms. The various forms of lymphocytes can be identified by antigens which these lymphocytes have on their surface. Monoclonal antibodies can be purchased from readily available sources which can identify types of lymphocytes from any particular population. Two such lymphocyte classes are T-Cells and B-Cells. B-Cells are generally responsible for the manufacture of specific antibodies. T-Cells have more variable functions and have been sub-classed into T-helper and T-suppressor cells. It is well known that patients afflicted with AIDS appear to have a viral infestation of the T-helper cells. AIDS thereby results in a gradual diminution in the number of T-helper cells. Additionally, for unknown reason, T-suppressor cells are increased in patients with AIDS.

When the ratio of T-helper to T-suppressor cells is reversed, the patient is less able to mount an immune response to other infectious agents such as *Pneumocystis carinii*, which is an agent responsible for pneumonia almost exclusively in patients with AIDS or other forms of immune suppression. Immune suppressed patients are also less able to mount a response to cells which have become transformed, which explains the lack of response of AIDS patients suffering from tumors such as Kaposi's sarcoma. Many investigators feel that agents capable of reversing T-helper cell deficiency and diminishing the overgrowth of T-suppressor cells hold promise as ultimate agents in the fight against the virus or agent responsible for AIDS, and various agents which have evidenced some ability to effect a reversal of T-helper deficiency and diminish T-suppressor overgrowth, such as Interferon, have been intensively studied.

SUMMARY OF THE INVENTION

Cytostatic alkaloid compounds which include alkaloids, alkaloid-phosphate derivatives, alkaloid-thiophosphate derivatives, known nitrogen- or phosphorus-containing cytostatic and carcinostatic agents (antimetabolites) coupled with alkaloids, alkaloid-phosphate derivatives or alkaloid-thiophosphate derivatives, and salts of such alkaloid compounds, particularly water soluble salts, and particularly thiolated derivatives of *Chelidonium majus L.* (greater celandine) alkaloids such as the thiophosphoric acid triaziridide ("Thio-TEPA") derivative of the alkaloid extracts of greater celandine whose hydrochloric acid salt is known by the trade name "Ukrain", are disclosed in each of my above-referenced earlier U.S. Pat. applications as being useful in diagnosing the presence of a tumor or tumor cells within a host, including a human host, and in providing a therapeutic method of treating such tumors or tumor cells or infections or infectious agents in vivo.

It has now been discovered that these cytostatic alkaloid compounds also demonstrate an ability to effect a reversal of T-helper deficiency and diminish T-suppressor overgrowth, and thus are useful in producing beneficial changes in immune responsiveness in human patients infected with the Human Immunodeficiency Virus (HIV) or having illnesses which compromise the ability to mount an effective immunological response, including AIDS.

It is therefore an object of this invention to provide a method of producing beneficial changes in immune responsiveness in human patients having illnesses which compromise the ability to mount an effective immunological response, including AIDS.

It is also an object of this invention to provide a therapeutic method of effecting a reversal of T-helper deficiency and a diminution of T-suppressor overgrowth in immune suppressed human patients.

A further object of this invention is to provide a therapeutic method of treating human patients suffering from AIDS-Related Complex ("ARC"), AIDS and associated illnesses.

These and other objects, as well as the nature, scope and utilization of this invention, will become readily apparent to those skilled in the art from the following description, the case history presented, and the appended claims.

BRIEF DESCRIPTION OF THE DRAWINGS

The following figures of the drawings designate the possible molecular structure based on elemental analysis of the products produced in the reaction between individual alkaloids and Thio-TEPA, cyclophosphamide and the like. In the description below, the respective alkaloid and phosphorus compounds are described after the numerical designation for the corresponding figure, followed by the actual and calculated elemental analysis for the product.

Calculated: C=49.44%; H=6.36% N=11.53%; P=8.49%.

Found: C=49.41%; H=6.34%; N=10.65%; P=8.67%.

FIG. 2. Chelerythrine+Thiophosphoric acid triaziridide $C_{66}H_{69}N_6O_{15}PS$.

Calculated: C=63.45%; H=5.56%; N=6.73%; P=2.47%. C=62.69%; H=5.37%; N=5.37%; P=2.35%.

Figure 1:
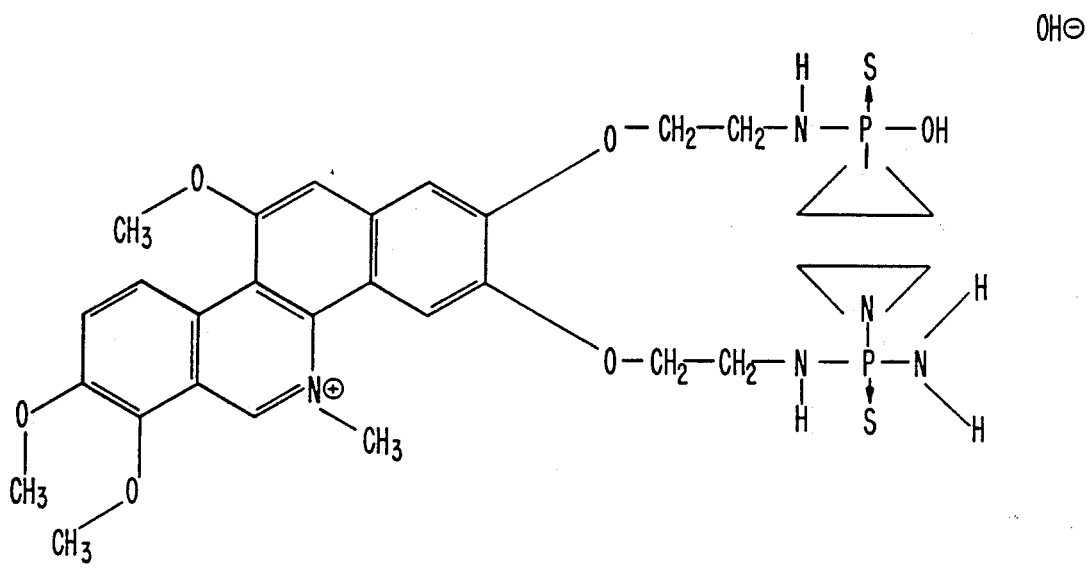
FIG. 1. Chelilutine+Thiophosphoric acid triaziridide (1-Chelilutine, 2-thiophosphoric acid triaziridide, 3-chelilutine+thiophosphoric acid triaziridice).
Figure 3:
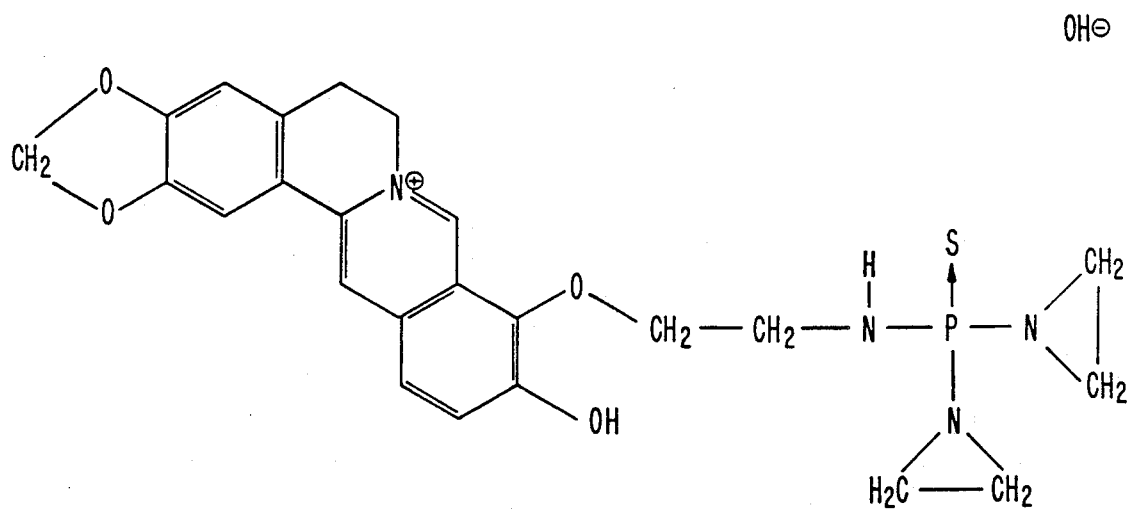

FIG. 3. Coptisine+Thiophosphoric acid triaziridide $C_{24}H_{27}N_4U_5PS$.

Calculated: C=56.02%; H=5.28%; N=10.88%; P=6.01%; S=6.23%.

Found: C=55.94%; H=5.12%; N=11.10%; P=5.89%; S=6.10%.

FIG. 4. Chelidonine+Thiophosphoric acid trizairidide $C_{66}H_{75}N_6O_{18}PS$.

Calculated: C=60.82%; H=5.79%; N=6.44%; P=2.37%; S=2.45%.

Found: C=61.41%; H=5.76%; N=5.94%; p=2.40%; S=2.39%.

Figure 5:
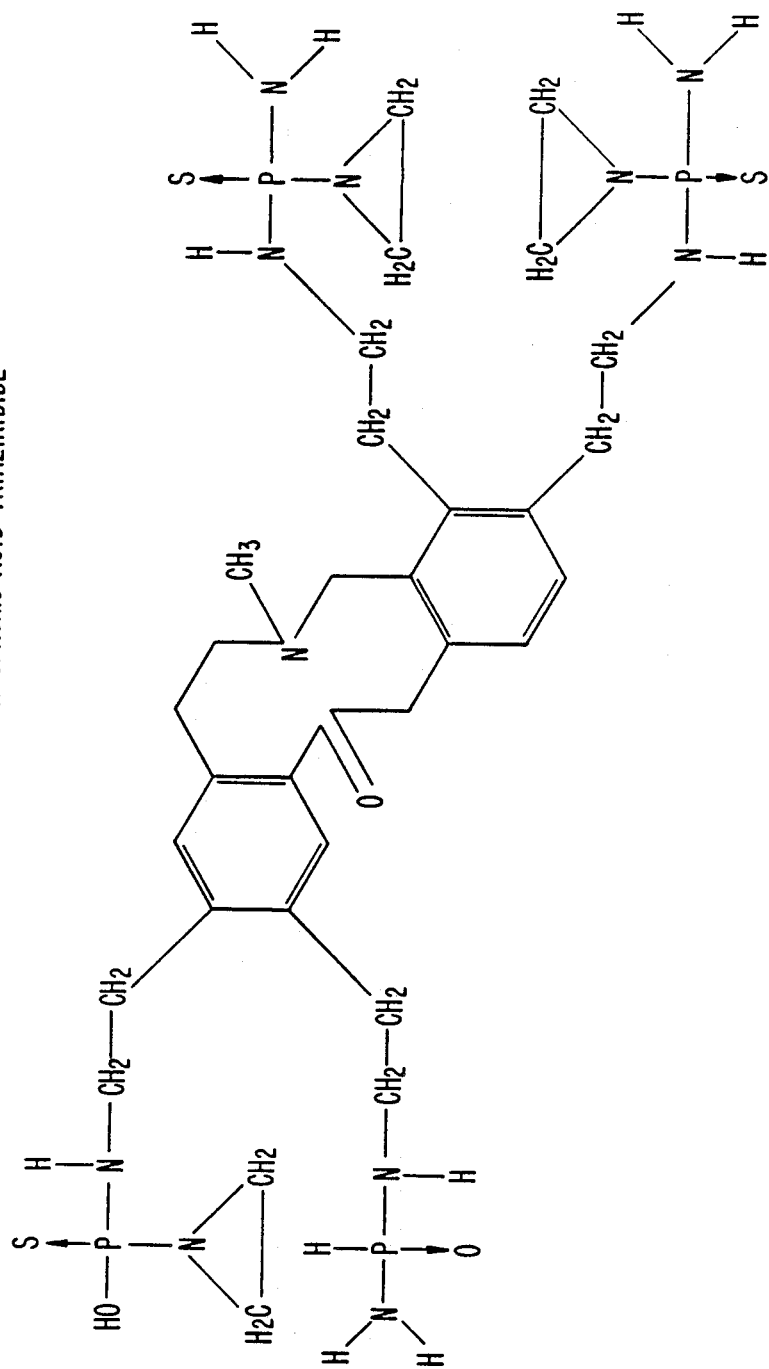

FIG. 5. Protopine-thiophosphoric acid triaziridide $C_{32}H_{55}N_{11}P_4S_3$.

Calculated: C=44.59%; H=6.43%; N=17.87%; P=14.37%; S=11.16%

Found: C=44.58%; H=6.14%5; N=17.76% C=44.72%; H=6.30%; N=17.77%; P=14.04%; S=12.71%.

Figure 6:
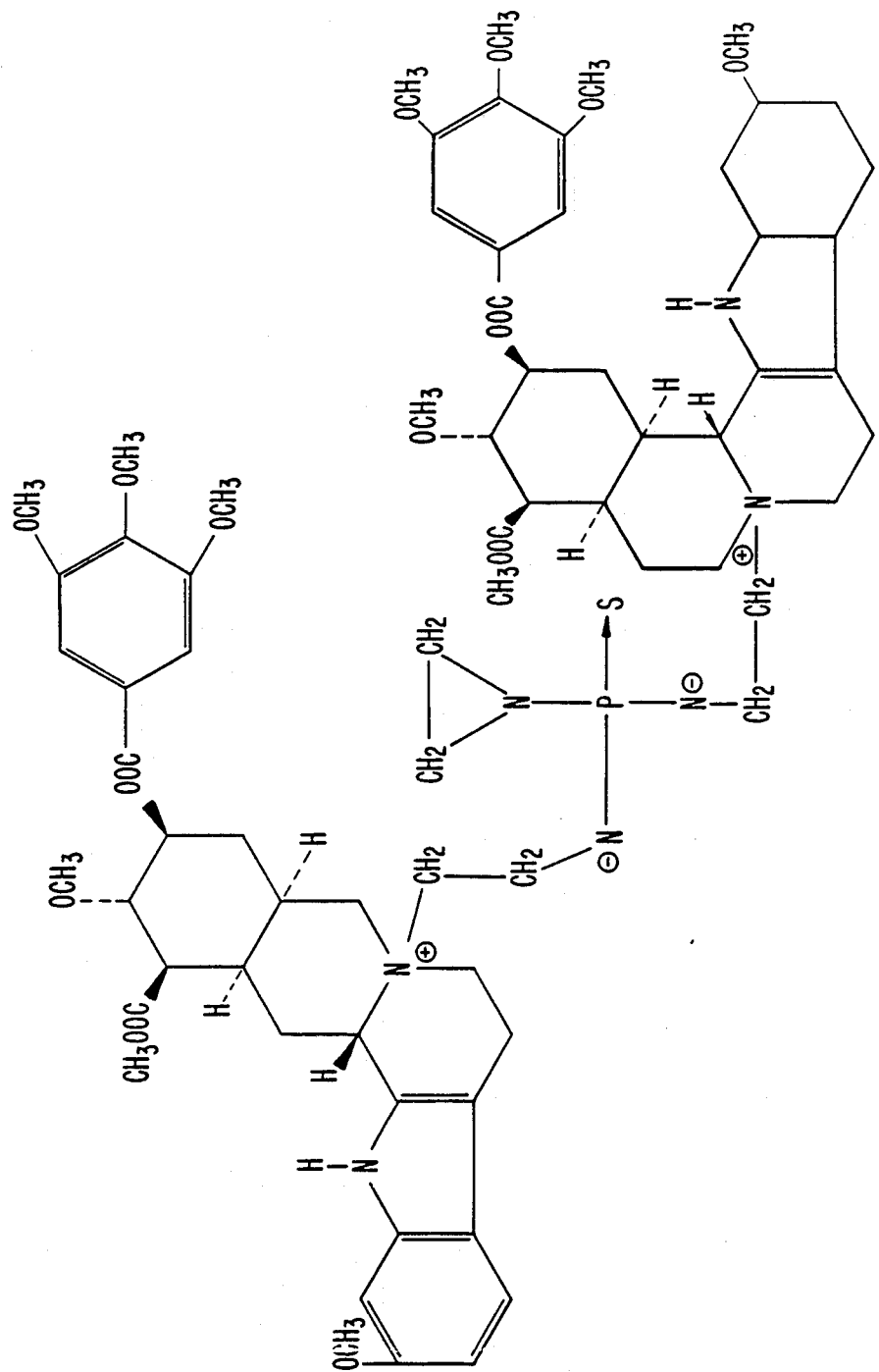

FIG. 6. Reserpine+thiophosphoric acid triaziridide $C_{72}H_{92}N_7PSO_{18}.2H_2O$, mp 120-125°.

Calculated: C=59.94%; H=6.70%; N=6.79%; P=2.14%; S=2.22%.

Found: C=59.89%; H=6.62%; N=6.82%; P=2.21%; S=2.26%.

Figure 7:
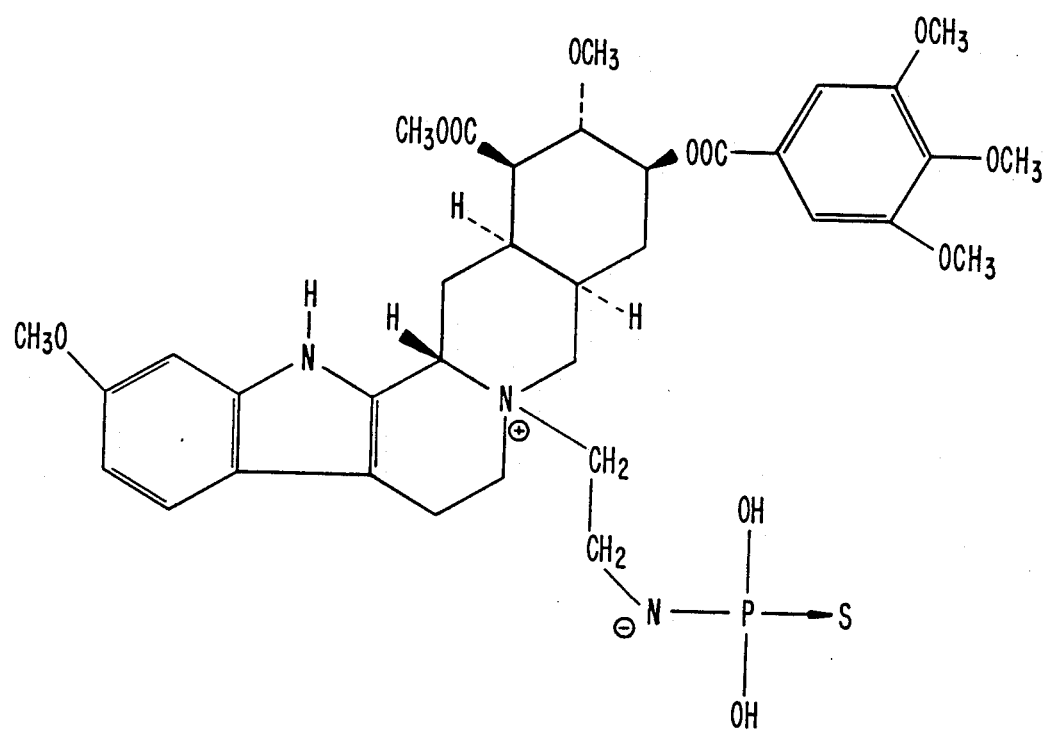

FIG. 7. Reserpine+thiophosphoric acid triaziridide $C_{35}H_{46}N_3O_{11}PS$.

Calculated: C=56.21%; H=6.20%; N=5.61%; P=4.14%; S=4.28%.

Found: C=56.3%; H=6.22%; N=4.11%.

Figure 8:
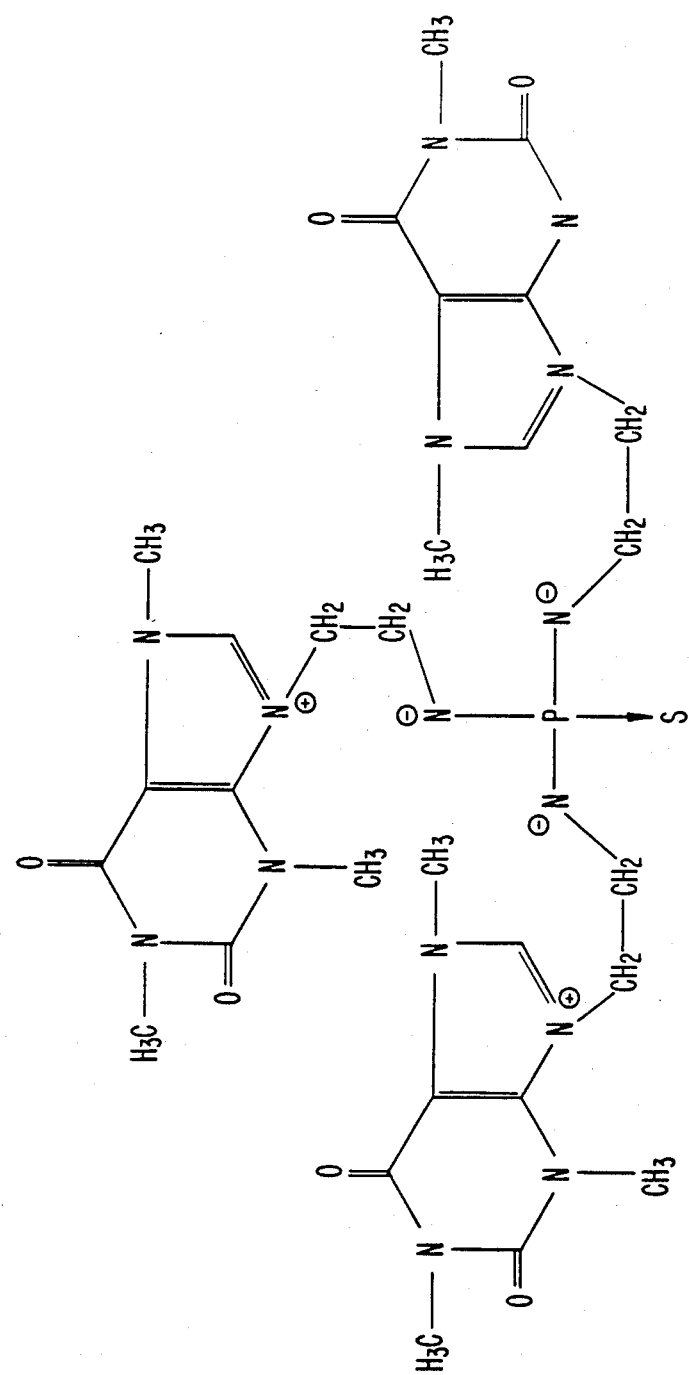

FIG. 8. Caffeine+thiophosphoric acid triaziridide $C_{30}H_{42}N_{15}PSO_6$, mp 110-112°; 215-216°.

Calculated: C=46.68%; H=5.48%; N=27.22%; P=4.01%; S=4.15%.

Found: C=47.37%; H-5.44%; N=27.25%; P=4.02%; S=4.15%.

Figure 9:
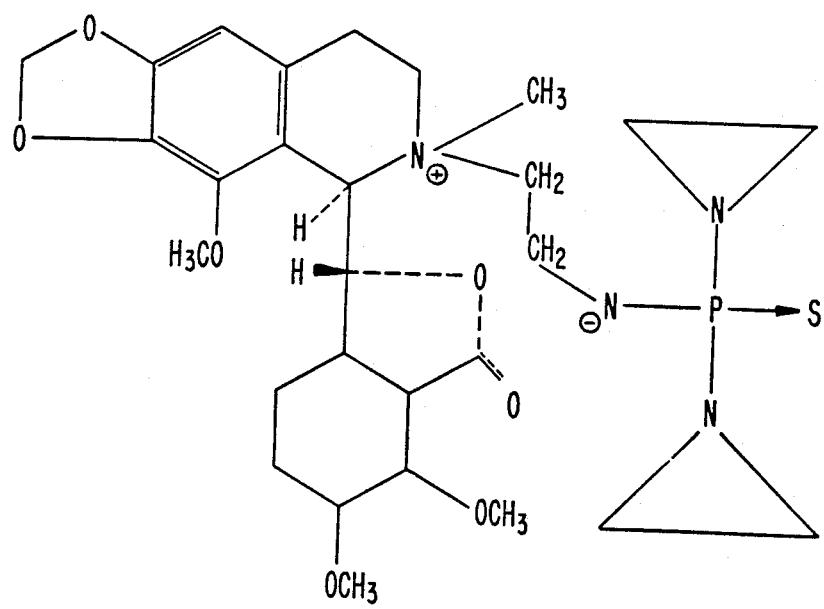

FIG. 9. Narcotine+thiophosphoric acid triaziridide $C_{28}H_{35}N_4PSO_7$, mp 225-226°.

Calculated: C=55.80%; H=5.85%; N=9.29%; p-5.13%; S=5.29%.

Found: C=55.34%; H=5.69%; N=9.52%; P=4.80%; S=5.29%.

Figure 10:
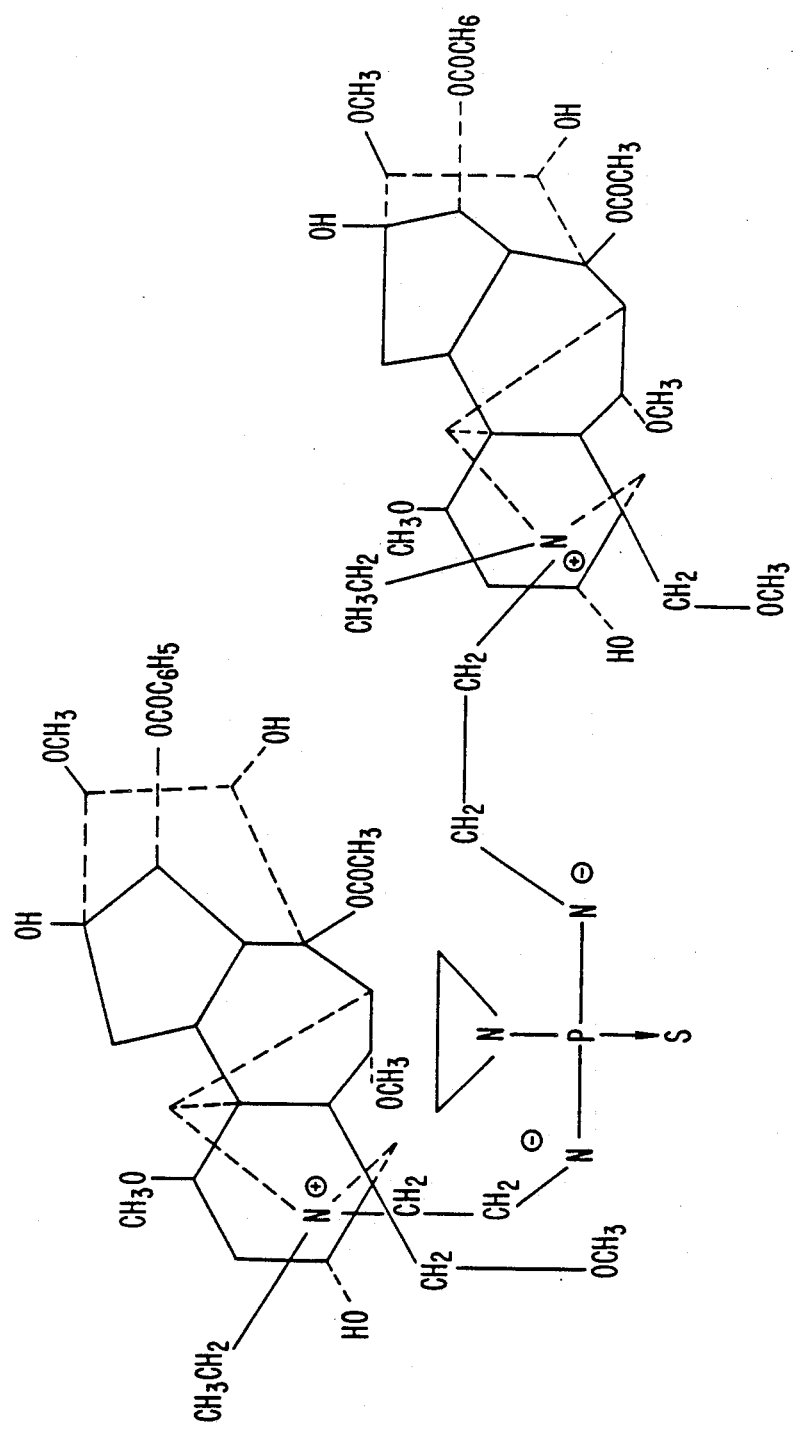

FIG. 10. Aconitine+thiophosphoric acid triaziridide $C_{74}H_{106}N_5O_2PS$, mp 197-200°.

Calculated: C=60.02%; H=7.21%%; N=4.72%; P=1.09%; S=2.16%.

Found: C=60.02%; H=7.21%; N=4.38%; P=2.09%; S=2.16%.

Figure 11:
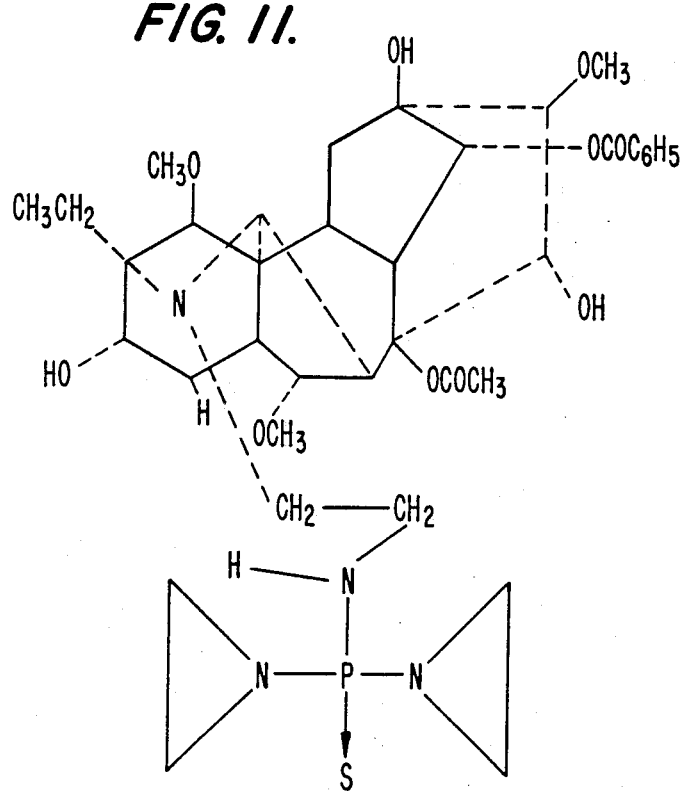

FIG. 11. Aconitine+thiophosphoric acid triaziridide $C_{39}H_{59}N_4O_{11}PS$, mp. 210-211°.

Calculated: C=56.92%; H=7.22%; N=6.80%; P=3.76%; S=3.86%.

Found: C=56.91%; H=7.12%; N=6.89%; P=3.60%; S=3.73%.

Figure 12:
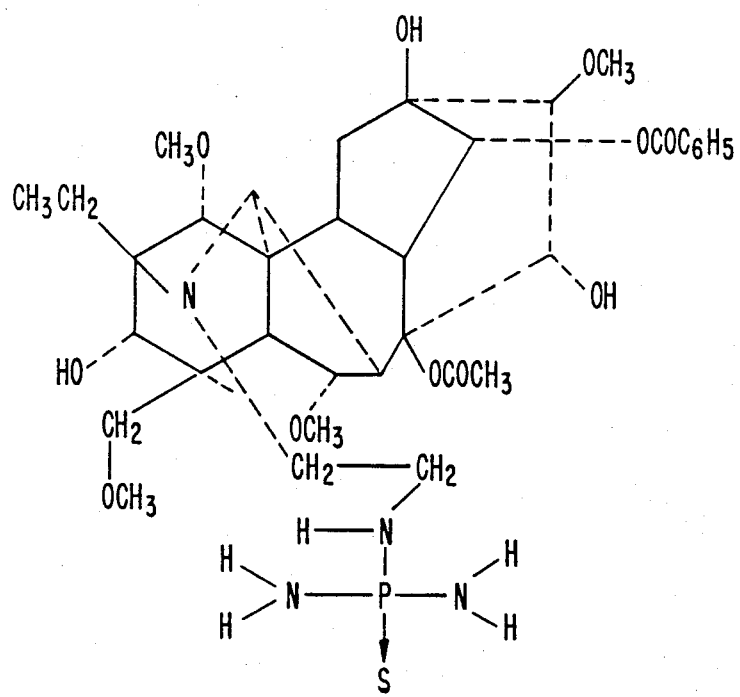

FIG. 12. Aconitine+thiophosphoric acid triaziridide $C_{35}H_{55}N_4PSO_{11}$, mp 190°-192°.

Calculated: C=54.83%; H=7.19%; N=7.26%.

Found: C=54.83%; H=6.98%; N=8.74%.

Figure 13:
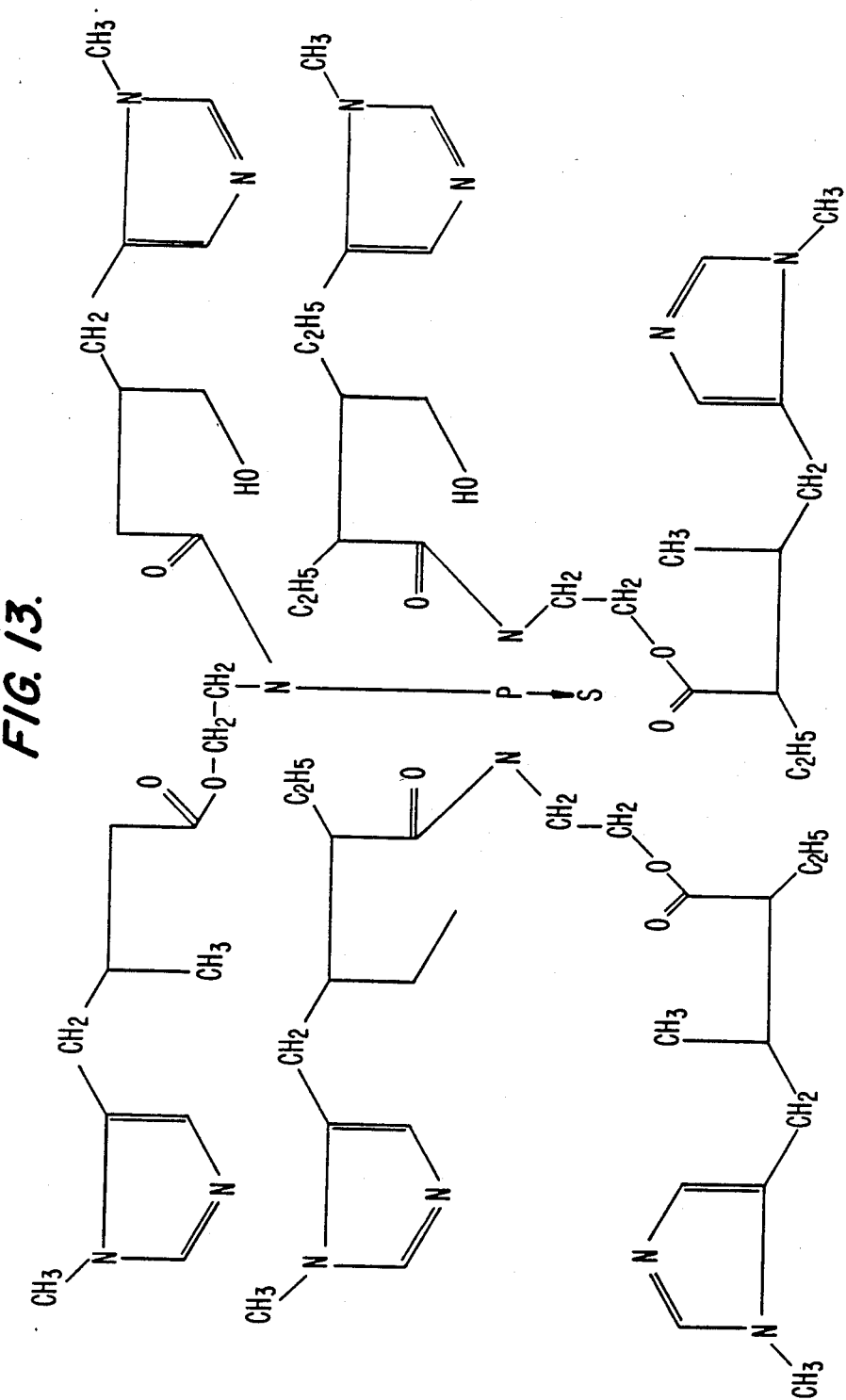

FIG. 13. Pilocarpine+thiophosphoric triaziridide $C_{26}H_{31}N_3O_7$.

Figure 14:
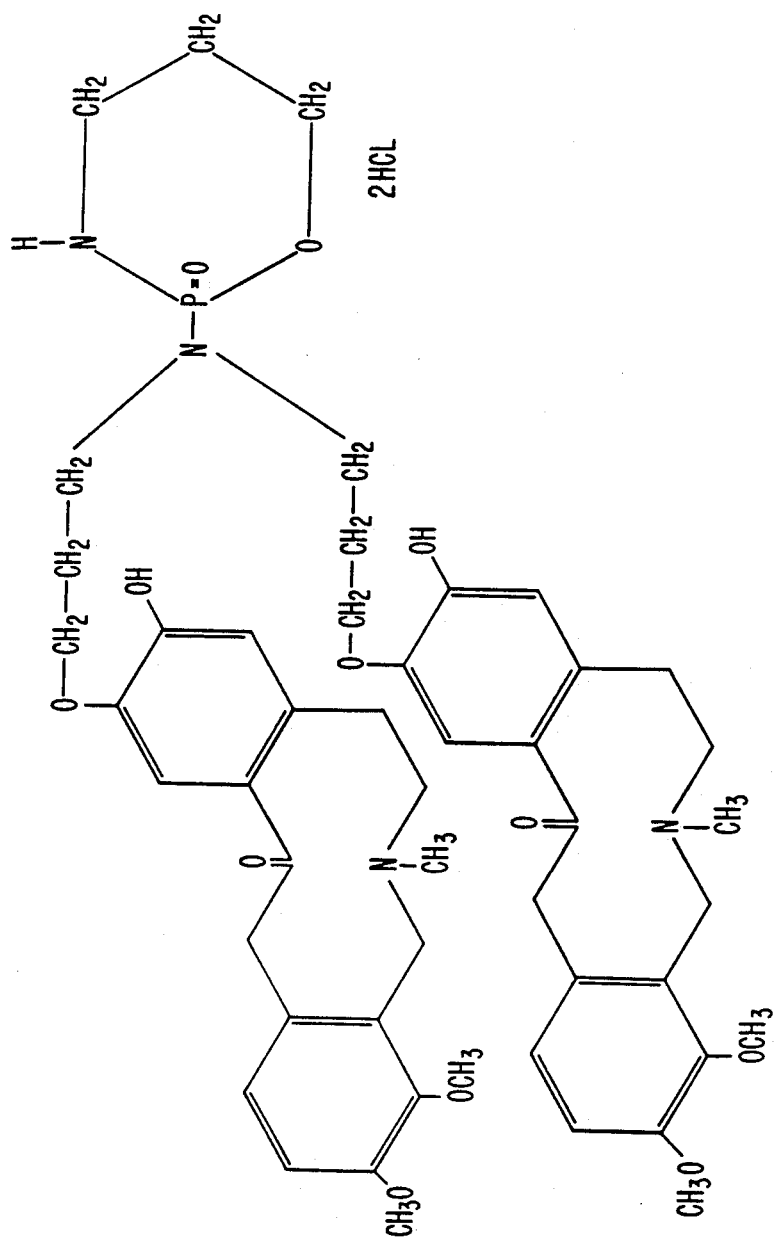

FIG. 14. Allocryptopine+cyclophosphamide [N,N-bis-($\beta$-chloroethyl)-N,O-propylenephosphoric acid ester diamide] $C_{49}H_{65}N_4O_{12}Cl_2P$, mp 159°-160°.

Calculated: C=8.25%; H=6.29%; N=5.58%; P=3.08%; Cl=7.06%.

Found: C=58.25%; H=6.25%: N=5.40%; P=2.53%; Cl-7.41%; C-54.84%; H=6.16%; N=5.62%; P=2.51%; Cl-7.26%.

Figure 15:
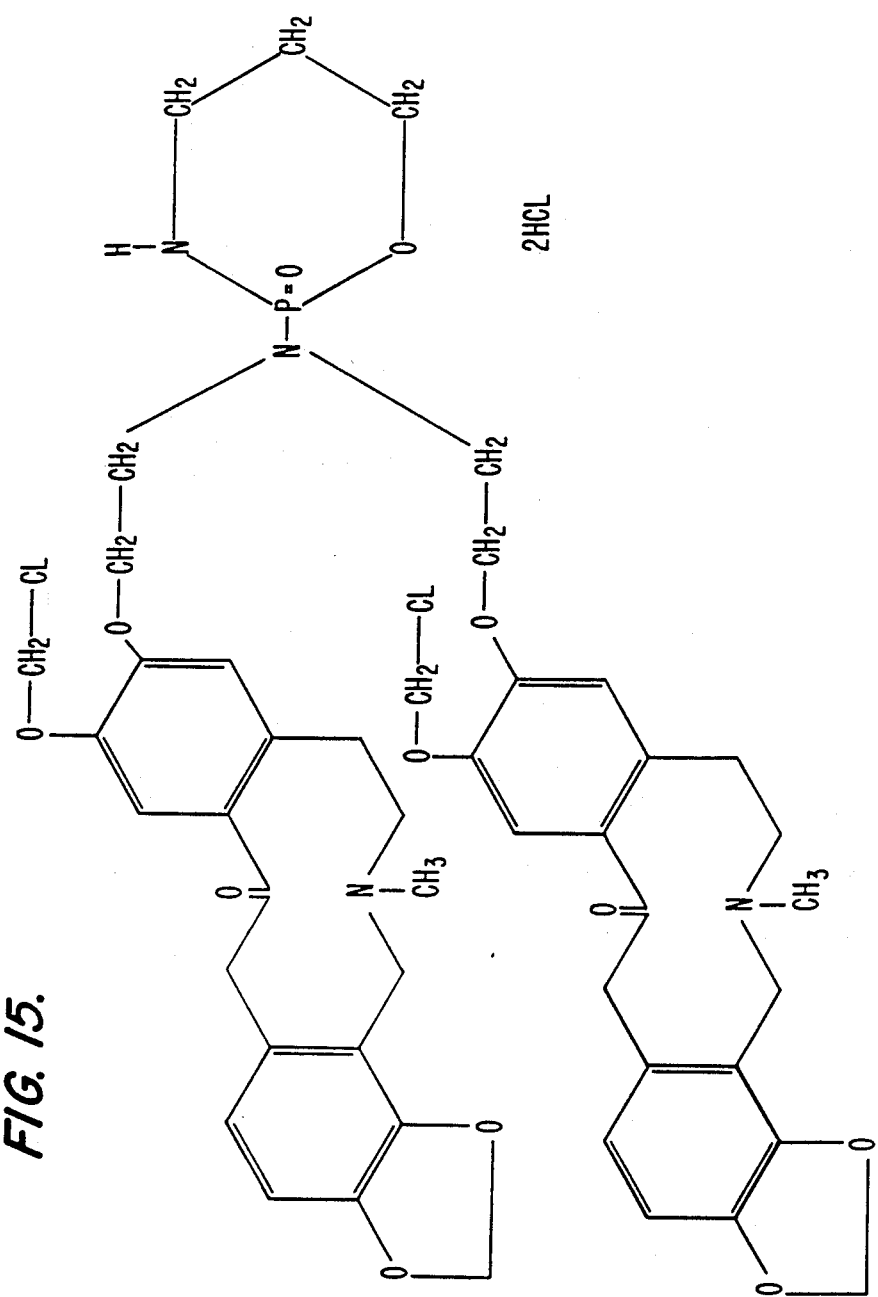
Figure 15A:
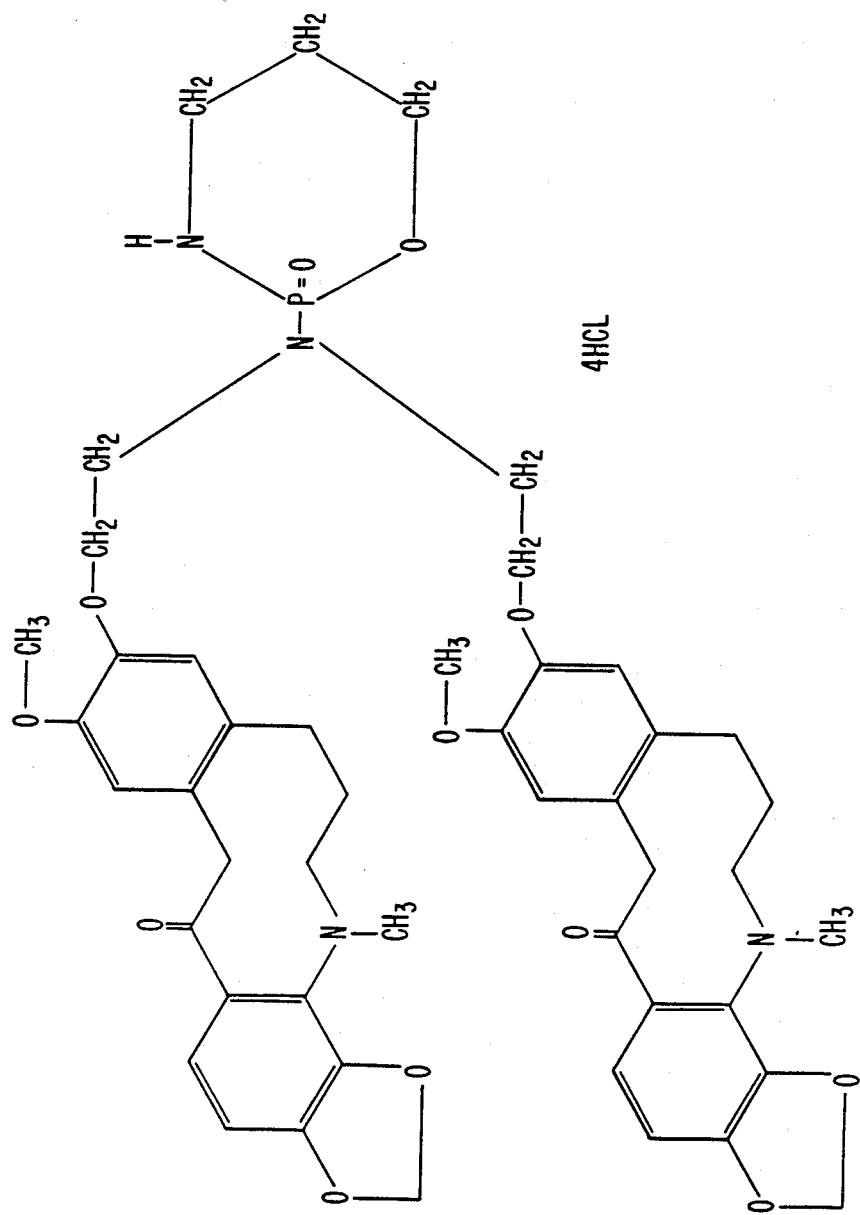
Figure 15B:
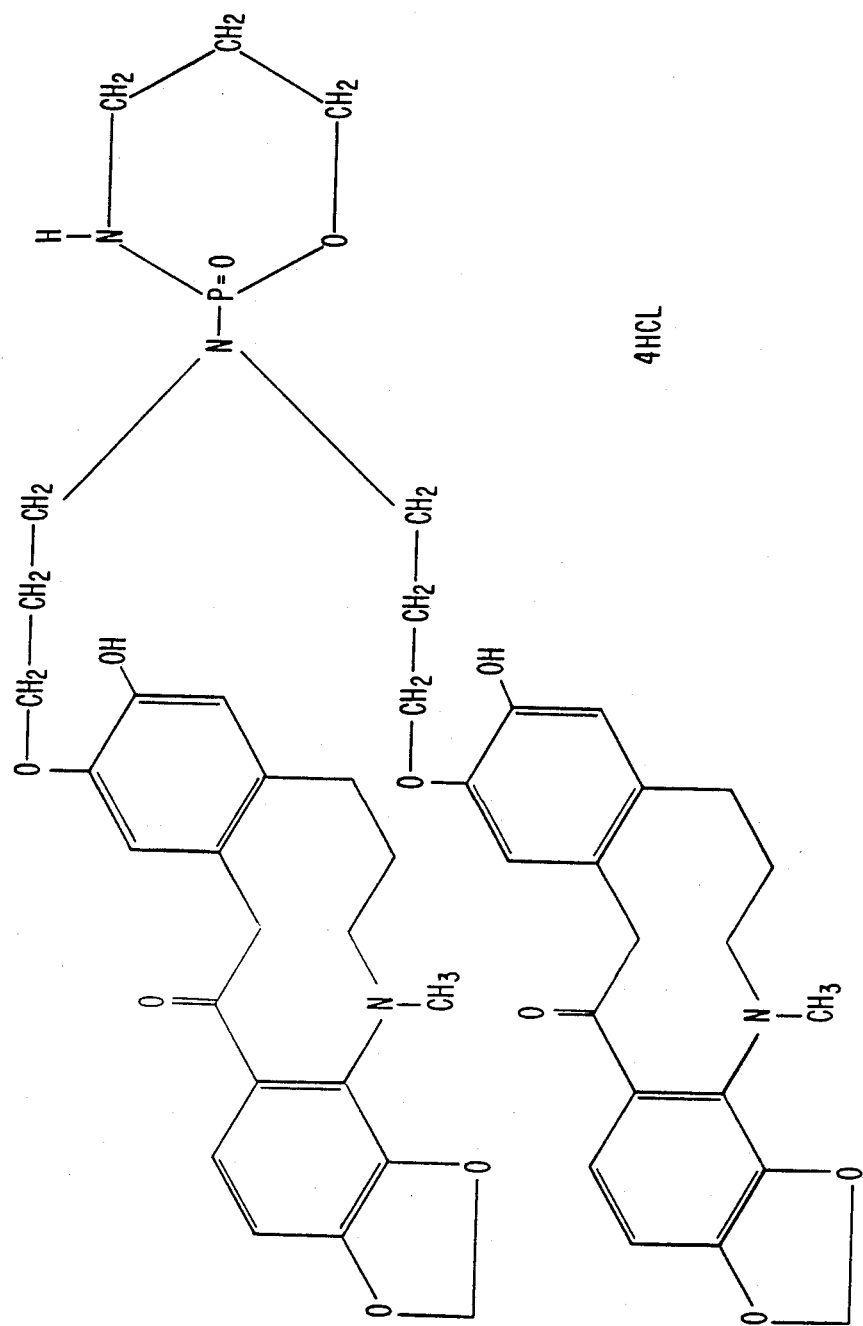

FIG. 15. Protopine +cyclophosphamide [N,N-bis-($\beta$-chlorethyl)-N,O-propylene phosphoric acid ester diamide] $C_{47}H_{55}N_4O_{12}PCl_4$, mp 239-242°.

Calculated: C=54.24%; H=5.32%; N=5.38%; P=2.97%; Cl=13.62%.

Found C=54.04%; H=5.25%; N=4.85%; P=2.72%; Cl=10.13%; C=54.48%; H-5.22%; N=4.69%; P=; Cl=9.91%.

FIG. 15$^a$. Protopine+cyclophosphamide [N,N-Bis'($\beta$-chlorethyl)-N',O-propylene phosphoric acid ester diamide] $C_{47}H_{59}N_4O_{12}PCl_4$, mp 239°-242°.

Calculated: C=54.03%; H=5.69%; N=5.36%; P=2.96%; Cl=13.57%.

Found: C=54.04%; H=5.25%; N=4.85%; P=2.27; Cl=10.13%; C=54.48%; H=5.22%; N=4.69%; Cl=9.91%.

FIG. 15$^b$. Protopine+cyclophosphamide [N,N-bis-($\beta$-chlorethyl)-N',O-propylenephosphoric acid ester diamide] $C_{47}H_{59}N_4O_{12}PCl_4$, mp 239°-242°.

Calculated: C=54.03%; H=5.69%;] N=5.36%; P=2.96; Cl=13.57%.

Found: C=54.04%; H=5.25%; N=4.85%; P=2.27%; Cl-10.13%; C-54.48%; H=5.22%; N=4.69%; Cl=9.91%.

Figure 16:
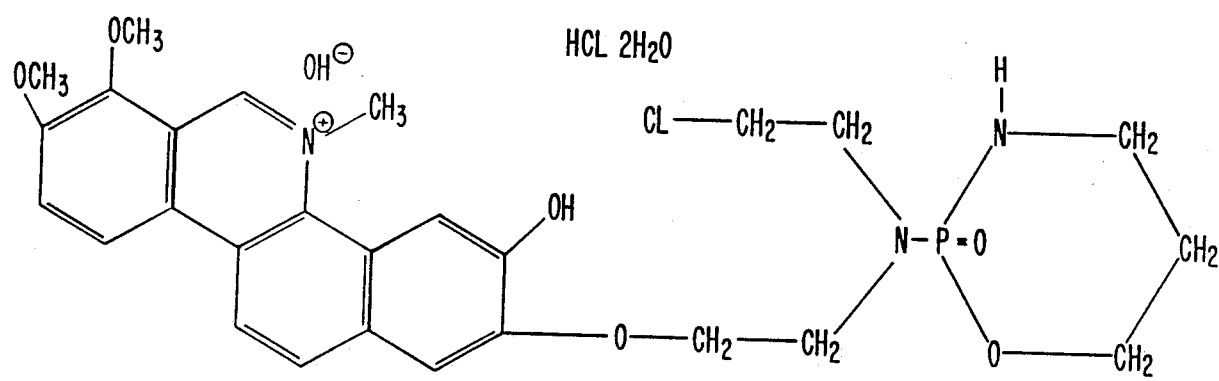

FIG. 16. Chelerythrine+cyclophosphamide [N,N-Bis-($\beta$-chlorethyl)-N',O-propylene phosphoric acid diamide] $C_{27}H_{37}N_3O_9PCl_2$, mp 188-192°.

Calculated: C=49.93%; H=5.74%; N=6.64%; P=4.76%; Cl=10.91%.

Found: C=49.85%; H=5.31%; N=6.06%; P=4.95%; Cl=13.23%; C=49.84%; H=5.24%; N=5.96%; Cl=14.24%.

Figure 17:
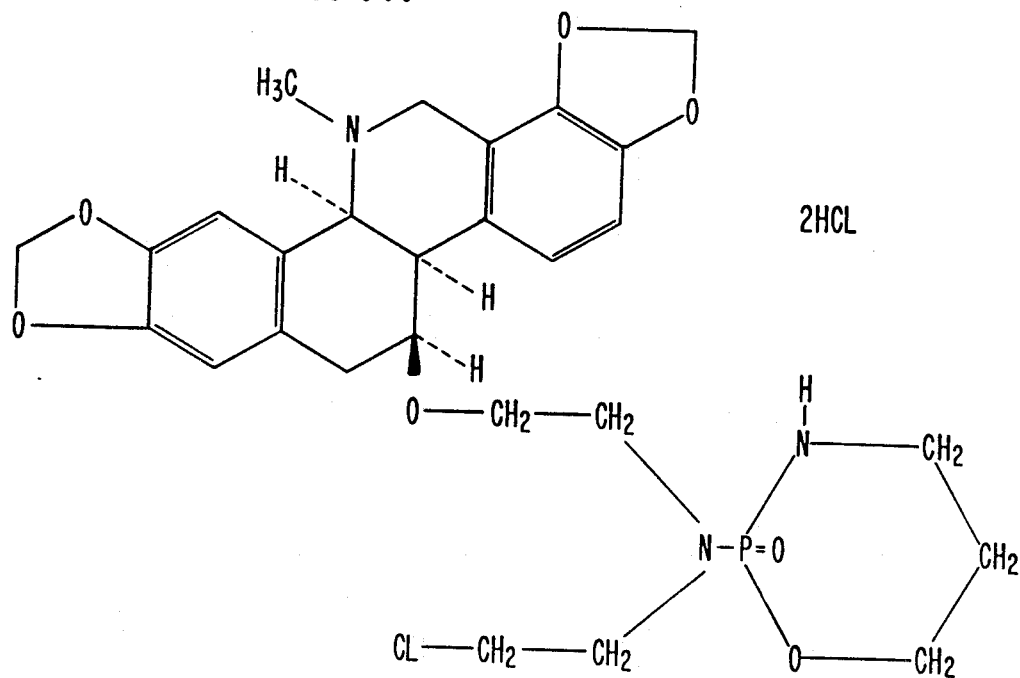

FIG. 17. Chelidonine+cyclophosphamide [N,N-Bis'($\beta$-chloroethyl)-N'O-propylene phosphoric acid ester diamide] $C_{27}H_{35}N_3O_7PCl_3$, mp 273°-276°.

Calculated: C=49.82%; H=5.41%; N=6.45%; P=4.75%; Cl=16.33%.

Found: C=49.26%; H=5.07%; N=5 12%; p=3.50%; Cl=16.50%.

If a mixture of different alkaloids is mixed with Thio-TEPA, three molecules of different alkaloids may be bound to one Thio-TEPA molecule and thus a large number of components may be synthesized. In this very complex mixture of reaction products, one or more of the reaction products can be responsible for the unique biological activity. Actually, more than 50 points fluorescent under UV-light resulted from the separation of the reaction products of Thio-TEPA and the alkaloid extract of Chelidonium Majus L. by two-dimensional thin-layer chromatography. Furthermore, it could be proven that no free ethylene groups of Thio-TEPA exist in the preparation of the reaction products produced from the alkaloid extract of Chelidonium majus L. reacted with Thio-TEPA. This proof based on chemical analysis, and biological tests to compare the lethal dose of Thio-TEPA which is 1 mg/kg body weight, whereas, a dose of 250 mg/kg body weight of the thio-TEPA derivative(s) of the alkaloid extract of Chelidonium majus L. is not toxic. Moreover, the preparation has no effect on leukemia 1210 and none on the blood picture. It can be derived from this that the ethylene groups of Thio-TEPA, which are also responsible for its toxic effect, are blocked in the reaction with alkaloids.

It is significant for diagnostic purposes that the hydrochloride salt of the reaction product(s) of Thio-TEPA and the alkaloid extract of *Chelidonium majus L.* has the property of being yellow-green fluorescent in ultraviolet light. The excitation frequencies lie within the frequency range from 220 to 490 nm. The spectral width of the fluorescence extends from 410 nm to 665 nm, while the maximum lies at 550 nm. This large spectral width is explained by the fact that the preparation is composed of a group of different alkaloid derivatives. The visibility limit of the fluorescence phenomenon under UV 366 nm on the plate for thin-layer chromatography lies at a dilution of 0.000007 mg/ml, 0.0000003 mg per 1 mm$^2$. The preparation also maintains this property in the living body, and thus, the distribution of the preparation could be observed in clinical experiments.

DETAILED DESCRIPTION OF THE INVENTION

In practicing this invention, a therapeutically effective amount of a cytostatic alkaloid compound which includes alkaloids, alkaloid-phosphate derivatives, alkaloid-thiophosphate derivatives, an alkaloid, alkaloid-phosphate or alkaloid-thiophosphate derivative coupled to a known nitrogen- or phosphorus-containing cytostatic or carcinostatic agent (antimetabolite), and salts of such alkaloid compounds, particularly water soluble salts, as disclosed in each of my above-referenced earlier U.S. Pat. applications, is preferably administered by parenteral injection, such as subcutaneous or intravenous injection.

The alkaloid compounds suitable for use in practicing this invention have the following characteristics: (1) stimulation of host cellular defense mechanisms, (2) efficacy in reducing or forestalling tumor growth or division as well as reducing or forestalling division or multiplication of host cells infected with viral agents, and/or (3) exhibiting enhanced concentration, or capacity for accumulation, in tumor cells or tumor tissue, and (4) pharmaceutical acceptability.

Among such alkaloid compounds are alkylated alkaloids derived from thiophosphoric acid which clinically and experimentally exhibit effectiveness in slowing cellular growth of tumor cells or cells infected with viral agents. Slowing cellular growth includes reductions in cellular activity or metabolism and reductions in cellular multiplication or division.

Water soluble salts of these alkaloid compounds can be made without sacrificing the alkaloid compound's cytostatic and carcinostatic properties by using pharmaceutically acceptable acids to form these salts. Berberine, sanguinarine, and other alkaloids from greater celandine can be made water soluble in this fashion.

Among the alkaloid compounds which can be used in practicing this invention are:

1. Bisbenzylisoquinoline alkaloids, such as curine, fangohinoline, tetrandine, penduline and thalidasine.
2. Aporphinebenzylisoquinoline alkaloids, such as thalicarpine.
3. Ibogo alkaloids, such as 20-hydoxyvoacamidine.
4. Indole-indoline alkaloids, such as leorosidine, lurosine, vinkaleukoblastine and leurocristine.
5. Tropolone alkaloids, such as colchicine.
6. Isoquinolone alkaloids, such as liriodenin, 0-methylatheroline, oxypurpurine, chelidonine, protopine, stylopine, allocryptopine, coptisine, chelerytrine, corysamine, chelidimerine, homochelidonine, methoxychelidonine, chelilutine, chelirubine, narciclasine, talicarpin, pakistanien, pacistanamine, pennsylvanine, pennsylvanamine, berberine, sanguinarine, caffeine, nitydyne and faraganine.
7. Steroid alkaloids.
8. Inidole isoquinoline alkaloids, such as 9-methoxyellipticin and ellipticin.
9. Indole alkaloids, such as reserpine.
10. Quinoline indolizidine alkaloids, such as campothecin.
11. Pyroline alkaloids, such as tatrofan.
12. Pyrolizidine alkaloids, such as heliotrin.
13. Acridone alkaloids, such as melicopin, acromycin and normelioepidin.
14. Phenanthroindolizidine alkaloids, such as tylophorine and tylocrebine.
15. Imidazole alkaloids, such as pilocarpine.
16. Quinolizidine alkaloids, such as matrin, oxymatrin and cryptoleurin.
17. Chinazolon alkaloids, such as febrifugin.
18. Benzazepin alkaloids, such as cephalotoxin, deoxyharringtonin, homoharringtonin and harringtonin.
19. Water soluble pharmaceutically acceptable salts of such alkaloid compounds.

The alkaloid-phosphate and alkaloid-thiophosphate derivatives useful in practicing this invention may also be used in the form of free bases. Examples of such known derivatives include thiophosphoric acid-di-(ethyleneimido)-N-berberinol-ethylamide and thiophosphoric acid-tri-(n-sanguinarinol)-ethylamide. Thiophosphoric acid amido derivatives may also be made from the alkaloids obtained from the condensed isoquinolines of *Chelidonium majus L.*

Especially suitable alkaloids for use in practicing this invention are those derived from greater celandine, such as those from condensed isoquinoline alkaloids (#6, above), which have been coupled to phosphorus containing organic compounds such as N, N', N''-triethylene-thiophosphoramide derivatives. Other such examples include the bases thiophosphoric acid-tri-(N-sanguinarinol)-ethylamine and thiophosphoric acid-di-(ethyleneimido)-N-berberinol-ethylamine.

Thiophosphoric acid derivatives of alkaloids such as those mentioned above are only sparingly soluble in water. These derivatives may be rendered water soluble, since water soluble derivatives are preferred for use in practicing this invention over, for example, derivatives soluble in organic solvents.

An alkaloid compound which is itself useful in practicing this invention may also be coupled to other carcinostatic or cytostatic agents, which compounds are already known in the art, preferably ones derived from alkylantiene antimetabolites, antibiotics, or other nitrogen- or phosphorus-containing organic compounds. The resulting coupled products may also be converted into pharmaceutically acceptable (non-toxic) salts for use in practicing this invention.

Examples of agents well known in the art of cancer chemotherapy which may be coupled to the aforementioned alkaloid compounds include nitrogen mustard gas, cyclophosphamide, triamcichon, chlorambucil, busulfan, nitomin, mannitol-nitrogen mustard gas, amthopterin, 6-mercaptopurine, 5-fluorouracil, cytosine-arabinoside, podophyllin, actinomycin C, mithramycin, actinomycin D, mitomycin C, adriamycin, bleomycin, asparaginase and ibenzmethycin. These chemotherapeutic agents or chemical modifications thereof can be depicted as:

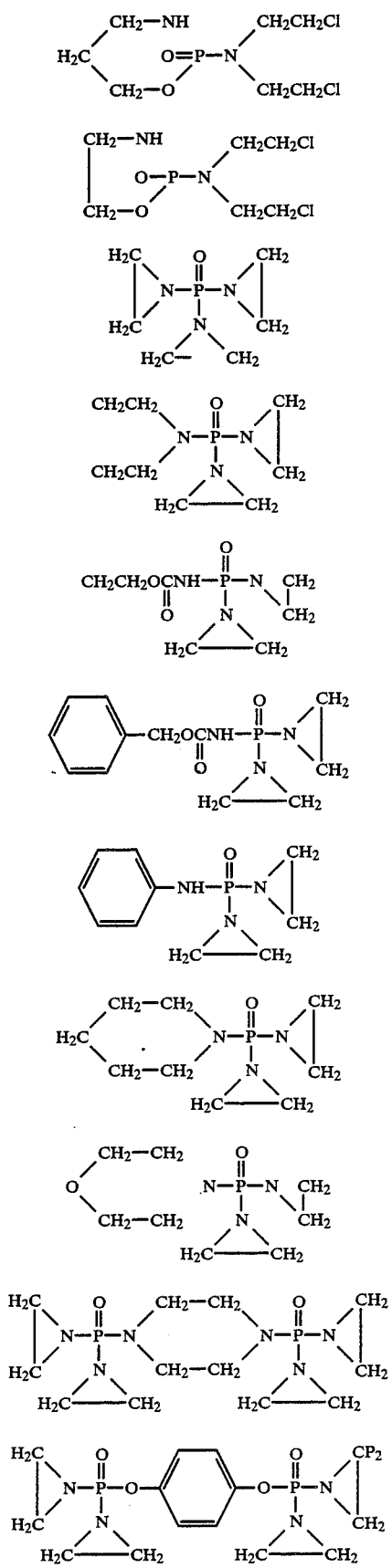
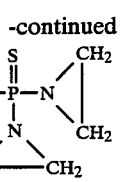
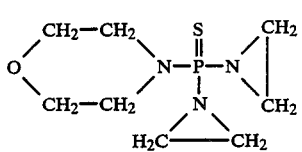
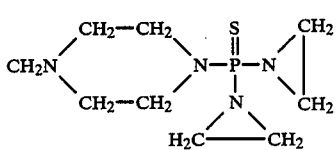
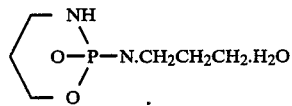
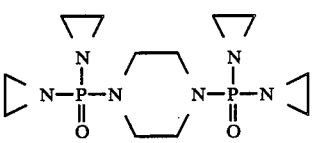
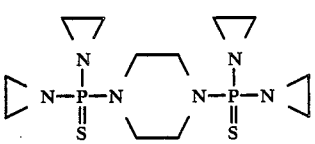
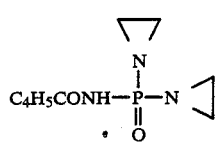
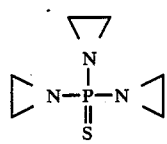
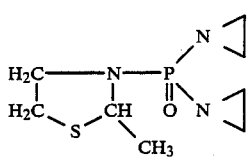
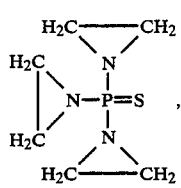

Of particular interest are those substances having the following formula:

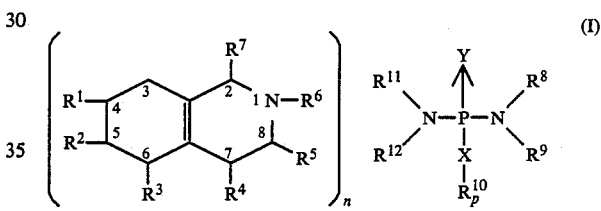

Phosphorus derivatives of the aforementioned alkaloids which are themselves useful in practicing this invention can be derived by coupling these alkaloids to the compounds depicted in formula I above. Especially preferred embodiments include coupled compounds such as those depicted where each of $R^1$, $R^2$, and $R^3$ is either a hydrogen atom or methoxy group, irrespective of the other.

Another especially preferred embodiment useful in practicing this invention can be derived by coupling the depicted compounds to an alkaloid wherein $R^1$ and $R^2$ and $R^3$ are each a methylenedioxy group;

Wherein $R^4$ and $R^5$ can be a hydrogen atom, or, together with the carbon atom to which they are depicted as being bonded, form a completely or partially hydrated phenyl or naphthyl group, which naphthyl or phenyl group can also be substituted with a methoxy, hydroxy or dioxymethyl group, rather than being completely or partially hydrated - especially when the $R^7$ is either a hydrogen atom (H), a double-bonded oxygen atom (=O), or an equal ring system bound over a keto chain ($CH_2$—CO—$CH_2$), and $R^{62}$ is CH (double bonds can be present in position 1, 2, and/or 7, and/or 8);

Or, wherein $R^6$ and $R^7$ together with the carbon or nitrogen atom to which they are respectively depicted as being bonded, form a partially hydrated benzene or napthol ring system which can be substituted, rather than being completely hydrated, with a methoxy, oxy or dioxymethyl group, especially when the carbon-nitrogen bond depicted between positions 1 and 2 is missing and $R^4$ and $R^5$ are hydrogen atoms;

$R^8 + R^9$ and $R^{11} + R^{12}$ mean $-CH_2-CH_2-$ and if $Y = S$, $X = N$ and $p = 2$, then $R^8 + R^9$ and $R^{11} + R^{12}$ is $R_2^3-CH_2-CH_2-$, $-CH_2-CH_2-O-CH_2-CH_2-$ or $$-CH_2-CH_2-\underset{\underset{CH_3}{|}}{N}-CH_2-CH_2-;$$

when $Y = S$, $X = N$, $n = 2$ represents $R_2^3-CH_2-CH_2-$,

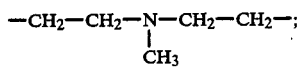

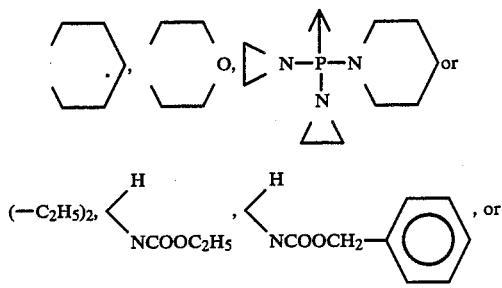

when $Y = S$, $X = O$, $n = 1$ means

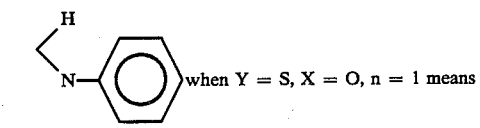 when when $Y = O$, $X = N$, $n = 1$ means 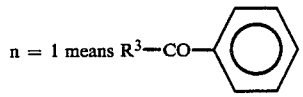

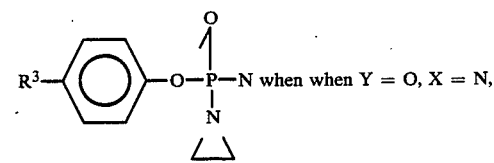 and when $Y = O$, $X = N$, $n = 2$ $R_2^3$ $Y = O$, $X = O$, $n = 1$, $R^8$ and $R^9$ each mean $-CH_2-CH_2-Cl$, $R^{11}$ H and $R^{10} + R^{12}$ mean $-CH_2-CH_2-$or $-CH_2-CH_2-CH_2$, when $Y = S$, $X = N$, $p = 1$, $R^3 -CH_2-CH_2-$ Salts of any of these phosphorus derivatives of the aforementioned alkaloids which are also useful in practicing this invention can be derived from any pharmaceutically acceptable acid which is itself water soluble to provide water soluble alkaloid derivatives. The preferred salt, for economic reasons, is hydrochloric acid.

The resulting alkaloid thiophosphoric acid amide salts do not differ in their cytostatic or carcinostatic properties from the original bases. The preferred salts are, however, easier to administer since preparation is easier and more precise, the salts being more water soluble. This avoids the disturbing side-effects which can be ascribed to the organic solvents necessary for the administration of the corresponding bases, which are water insoluble and must, therefore, be administered in such organic solvents.

Hydrochloride salts of the aforementioned alkaloids, especially berberine, sanguinarine, or other alkaloids from greater celandine, may be coupled with the following compounds:

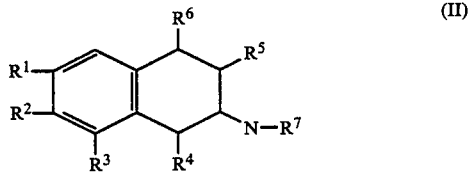

The alkaloids themselves may similarly be coupled with the aforementioned compounds, well known in the chemotherapy art, which are themselves cytostatic or carcinostatic.

Such cytostatic- or carcinostatic-coupled alkaloid derivatives can be prepared in either of two ways. Generally, such coupling reactions, or conversion of the alkaloid salts, are carried out in a solvent mixture containing the aforementioned compounds at elevated temperatures, such as reflux temperature. Alternatively, the alkaloid base can first be coupled with the cytostatic or carcinostatic coupling reagent, such as a thiophosphoric acid amide, and subsequently converted into the salt. Such subsequent conversion can be, for example, by saturating a solvent solution of the alkaloid derivative, in base form, with hydrogen chloride gas and allowing such saturated solution to stand. Such a reaction of the alkaloid with the cytostatic or carcinostatic compound is best carried out in an organic solvent where, after salt formation is accomplished, the resultant salt will precipitate out of the organic solvent. The salt can also be separated into an aqueous phase simply by adding water or hydrated acid to the organic solvent and shaking. The particular organic solvent used will vary with the particular alkaloid. By way of example, it is noted that benzene, anhydrous dioxane and a mixture of anhydrous ether and dichloroethane have been successfully used as solvents to prepare thiophosphoric acid-tri-(N-sanguinarinol)-ethyl amide, berberine hydrochloride, and the mixture of an extract of greater celandine and thiophosphoric acid-triethylene amide.

The actual alkaloid component of any administered composition used in practicing this invention may beneficially consist of one or more than one of the aforementioned alkaloid compounds.

A particular preparation for practicing this invention, for example, consists of alkaloids from *Chelidonium majus L.* which have been alkylated with, for example, thiophosphoric acid triaziridide. Since Thio-TEPA has three possible reactive groups of which any may (1) bind to the alkaloid molecule, or (2) be substituted with hydoxy (OH) or ammonia groups (NH$_2$), a whole series of different reaction products may actually arise. In order to examine more carefully the actual reaction products, a single alkaloid, chelidonine, was purified from greater celandine. When chelidonine is reacted with Thio-TEPA, cyclophosphamide, or other test compounds, at least twelve different reaction products can be identified by thin layer chromatography. Some of these twelve products have been isolated, crystallized and subjected to elemental analysis, as described hereinabove in the "BRIEF DESCRIPTION OF THE DRAWINGS".

These cytostatic alkaloid derivatives are disclosed in each of my above-referenced earlier U.S. Pat. applications to stimulate the patient's cellular defense mechanism and to be antagonistic to cells which have been attacked by virus and other antigens. In addition, it was disclosed in my aforementioned copending U.S. Pat. application:

". . .that in the case of very many patients, infections disappeared after the first Ukrain injection. Among them were stubborn mycosis which previously had not responded to any therapy, cases of chronic bronchitis and throat inflammations of unclear genesis, as well as other viral and bacterial diseases, according to the treating physicians. Thus, the previous results [given in this application] also suggest the stimulation of lymphocytes to immunocytes by means of the Preparation: such stimulation is equivalent to the production of the so-called killercells which destroy the affected tissue or the tissue foreign to the body, or virus which has penetrated healthy cells, and/or bacteria, fungi, and the like. Therefore, the healing of tumor diseases, as well as viral diseases, bacterial diseases and fungal diseases, and in addition a healing of polyarthritis can be realized."

Furthermore, as also shown in my aforementioned copending U.S. Pat. application:

"To determine the effect of the mechanism of therapeutic and diagnostic capacity of Ukrain, studies were carried out concerning the immuno-stimulating effect of Ukrain in vitro in the so-called lymphocyte-transformation test, and results of the studies are reported in the following tables. Generally, lymphocytes are known to be immunocompetent when they are capable of recognizing the specific antigen or if they are capable reacting with it. Such cells are called immunocytes and their successors are called immunoblasts.

The formation of immunoblasts can also be carried out in vitro. The immunoblasts have a size of 20–30μ, whereas, normal lymphocytes have a size of only 5–15μ. In the following immunological tests, isolated lymphocytes of healthy humans and of guinea pigs were used for the blast transformation after the addition of Ukrain. A mixture of the compound known under the tradename Ficoll 4000 and EDTA was used for the isolation (0.9 DTA+0.1 Ficoll 4000).

The isolated lymphocytes were grown in vitro in Parker solution, with an addition of 1.6μg, 0.16μg and 0.016μg. At the same time lymphocytes were bred in Parker solution with 5μg/ml of the unspecific stimulator phytohemaglutinin (PHA) and without an additive as a control run. In order to avoid solonization of bacteria, effective amounts of antibiotics, penicillin, streptomycin and nystatin, were added. The cultures were incubated at 37° C. and the number of transformed lymphocytes was counted daily under the microscope for 3 days.

100 lymphocytes were counted out in each preparation and those lymphocytes which were larger than 15μ (from humans) and larger than 20μ in the case of guinea pigs were evaluated as being transformed. In all cases, before the beginning of breeding, the number of transformed cells was not larger than 10.1%. The tests were carried out with the lymphocytes of 10 healthy humans and 10 healthy guinea pigs.

Since in the case of a cure with Ukrain the average single dose amounts to 10 mg (the mean individual dose of Ukrain used in these experiments being 16 mg), the dose of Ukrain was actually 1/10000; 1/100000 and 1/1000000 of the amount. The results are summarized in the following Tables I and II.

TABLE I

| No. | Culture-medium With Additive | Breeding Time | | |
|---|---|---|---|---|
| | | 24 hrs. | 48 hrs. | 72 hrs. |
| 1. | 1.6* | 48.6 | 45.6 | 40.2 |
| | 0.16* | 42.3 | 29.3 | 28.5 |
| | 0.016* | 35.6 | 33.6 | 25.0 |
| | PHA | 32.2 | 28.3 | 27.9 |
| | Without stimulator | 19.2 | 15.3 | 1.8 |
| 2. | 1.6* | 53.9 | 30.2 | 18.3 |
| | 0.16* | 48.7 | 32.2 | 32.00 (?) |
| | 0.016* | 27.3 | 30.2 | 18.5 |
| | PHA | 20.8 | 17.2 | 17.5 |
| | Without stimulator | 13.3 | 12.2 | 19.2 (?) |
| 3. | 1.6* | 50.2 | 48.3 | 42.8 |
| | 0.16* | 49.3 | 51.1 | 39.9 |
| | 0.016* | 41.0 | 29.3 | 30.1 |
| | PHA | 32.5 | 29.8 | 22.3 |
| | Without stimulator | 18.0 | 11.2 | 10.3 |
| 4. | 1.6* | 55.6 | 42.3 | |
| | 0.16* | 50.8 | 40.7 | 43.8 |
| | 0.016* | 41.2 | 38.5 | 39.5 |
| | PHA | 33.2 | 27.0 | 18.0 |
| | Without stimulator | 18.2 | 18.0 | 16.2 |
| 5. | 1.6* | 51.3 | 43.5 | 31.5 |
| | 0.16* | 48.2 | 33.2 | 33.5 |
| | 0.016* | 39.9 | 31.5 | 30.2 |
| | PHA | 33.4 | 20.3 | 11.3 |
| | Without stimulator | 12.5 | 12.5 | 8.4 |
| 6. | 1.6* | 58.5 | 57.9 | 41.8 |
| | 0.16* | 48.3 | 50.0 | 43.2 |
| | 0.016* | 40.1 | 35.2 | 30.0 |
| | PHA | 30.2 | 22.1 | 17.3 |
| | Without stimulator | 19.0 | 18.2 | 13.5 |
| 7. | 1.6* | 43.3 | 41.2 | 39.8 |
| | 0.16* | 42.3 | 36.6 | 36.2 |
| | 0.016* | 41.2 | 37.2 | 35.5 |
| | PHA | 33.3 | 33.4 | 27.2 |
| | Without stimulator | 15.1 | 16.1 | 13.2 |
| 8. | 1.6* | 48.7 | 45.1 | 40.3 |
| | 0.16* | 43.1 | 39.2 | 31.1 |
| | 0.016* | 35.6 | 29.8 | 24.2 |
| | PHA | 31.3 | 27.0 | 24.3 |
| | Without stimulator | 12.2 | 10.1 | 10.5 |
| 9. | 1.6* | 53.3 | 51.5 | 41.2 |
| | 0.16* | 49.6 | 47.2 | 42.2 |
| | 0.016* | 39.2 | 36.7 | 34.6 |
| | PHA | 38.3 | 32.8 | 25.2 |
| | Without stimulator | 18.1 | 16.7 | 11.3 |
| 10. | 1.6* | 56.2 | 53.6 | 40.7 |
| | 0.16* | 49.3 | 42.8 | 34.5 |
| | 0.016* | 39.8 | 37.3 | 28.3 |
| | PHA | 34.2 | 33.2 | 27.5 |
| | Without stimulator | 12.0 | 10.2 | 8.4 |

*Amount of Ukrain in units of μg/ml.

TABLE II

| | Percentage of transformed human lymphocytes. | | | |
|---|---|---|---|---|
| No. | Culture-medium With Additive | Breeding Time | | |
| | | 24 hrs. | 48 hrs. | 72 hrs. |
| 1. | 1.6* | 47.2 | 43.4 | 41.2 |
| | 0.16* | 43.8 | 39.2 | 38.6 |
| | 0.016* | 39.6 | 36.7 | 35.2 |
| | PHA 5 μg/ml | 36.6 | 24.8 | 20.8 |
| | Without stimulator | 11.1 | 9.2 | 9.0 |
| 2. | 1.6* | 49.9 | 41.2 | 37.2 |
| | 0.16* | 43.2 | 40.3 | 33.2 |
| | 0.016* | 38.6 | 36.2 | 26.8 |
| | PHA 5 μg/ml | 31.2 | 28.0 | 21.2 |
| | Without | | | |

TABLE II-continued

Percentage of transformed human lymphocytes.

| No. | Culture-medium With Additive | Breeding Time 24 hrs. | 48 hrs. | 72 hrs. |
|---|---|---|---|---|
|  | stimulator | 18.4 | 14.1 | 8.4 |
| 3. | 1.6* | 19.1 | 18.8 | 16.2 |
|  | 0.16* | 19.5 | 18.2 | 15.3 |
|  | 0.016* | 14.2 | 15.3 | 13.2 |
|  | PHA 5 μg/ml | 33.1 | 28.2 | 14.1 |
|  | Without stimulator | 10.7 | 9.3 | 15.3 |
| 4. | 1.6* | 43.9 | 42.8 | 39.4 |
|  | 0.16* | 41.2 | 40.6 | 41.2 |
|  | 0.016* | 33.6 | 32.1 | 31.2 |
|  | PHA 5 μg/ml | 40.2 | 33.6 | 28.3 |
|  | Without stimulator | 13.6 | 12.3 | 10.8 |
| 5. | 1.6* | 53.3 | 51.5 | 47.8 |
|  | 0.16* | 48.6 | 43.6 | 41.0 |
|  | 0.016* | 37.2 | 37.8 | 36.2 |
|  | PHA 5 μg/ml | 36.4 | 28.5 | 25.4 |
|  | Without stimulator | 15.3 | 14.4 | 12.8 |
| 6. | 1.6* | 55.5 | 53.4 | 51.5 |
|  | 0.16* | 51.2 | 49.1 | 47.3 |
|  | 0.016* | 43.2 | 36.2 | 36.0 |
|  | PHA 5 μg/ml | 37.1 | 36.2 | 34.7 |
|  | Without stimulator | 19.3 | 18.4 | 16.5 |
| 7. | 1.6* | 48.6 | 46.8 | 42.5 |
|  | 0.16* | 47.2 | 45.2 | 24.3 |
|  | 0.016* | 39.8 | 32.0 | 21.2 |
|  | PHA 5 μg/ml | 30.1 | 26.8 | 19.0 |
|  | Without stimulator | 14.7 | 13.1 | 8.5 |
| 8. | 1.6* | 52.3 | 37.4 | 21.8 |
|  | 0.16* | 48.3 | 28.3 | 19.3 |
|  | 0.016* | 41.2 | 19.4 | 17.4 |
|  | PHA 5 μg/ml | 37.3 | 19.5 | 20.1 |
|  | Without stimulator | 9.0 | 8.3 | 8.2 |
| 9. | 1.6* | 47.2 | 32.8 | 29.1 |
|  | 0.16* | 43.4 | 36.4 | 34.2 |
|  | 0.016* | 38.6 | 25.0 | 20.0 |
|  | PHA 5 μg/ml | 36.2 | 28.6 | 21.4 |
|  | Without stimulator | 15.3 | 13.3 | 10.7 |
| 10. | 1.6* | 48.3 | 37.4 | 33.3 |
|  | 0.16* | 43.4 | 41.2 | 36.8 |
|  | 0.016* | 37.1 | 36.2 | 29.1 |
|  | PHA 5 μg/ml | 30.0 | 19.4 | 18.4 |
|  | Without stimulator | 9.3 | 9.6 | 5.3 |

*Amount of Ukrain in units of μg/ml.

In the test a statistically significant difference was shown between the number of transformed lymphocytes of humans and of animals and of control groups absent Ukrain. The conclusion can be drawn from this that the preparation Ukrain has an immunological effectiveness and stimulates the human defense mechanism. Clear transformation of lymphocytes did not occur in only one out of 10 cases (see Table II, No. 3, where human lymphocytes were tested. In the case of patient no. 3, under certain circumstances an "in vitro equivalent" could exist for the clinical phenomenon, in which individual patients showed no reaction at all to Ukrain).

Although no clear lymphocyte transformation was effected by Ukrain in the case of test person no. 3, a higher lymphocyte transformation was obtained with all other patients than with PHA."

The effective amount of alkaloid or alkaloid derivative administered when practicing this invention will vary depending on a number of factors customarily considered in therapeutic settings: the body weight of the patient, the stage of the disease and consequent condition of the patient, the pharmaceutical acceptability of the alkaloid compound administered (the patient's tolerance for the particular alkaloid compound and dosage level chosen), etc. In general, however, the total dosage amount administered will be an amount sufficient to reverse T-helper cell deficiency and diminish the overgrowth of T-suppressor cells in the patient, a result readily measurable in known manner by monoclonal antibody assay of lymphocyte subpopulations. Individual doses can range from about 0.5 mg or less to about 680 mg or more. The alkaloid or alkaloid derivative, as indicated above, generally will be administered in solution, and preferably as an aqueous solution containing, for example, 0.5 mg of the alkaloid or alkaloid derivative diluted in 1 ml of saline solution. The total amount of alkaloid or alkaloid derivative administered when practicing this invention can be determined in each case by analysis of its effect on the progress of the disease, e.g., by determining in known manner T-helper and T-suppressor levels or increases in immune response to other infectious agents.

In order that those skilled in the art can more fully understand this invention, the following example is set forth. This example is given solely for purposes of illustration, and should not be considered as expressing limitations unless so set forth in the appended claims.

EXAMPLE

A patient found to be HIV positive developed, three months later, symptoms of AIDS with weakness, fatigue, weight loss and loss of appetite. His lymph nodes were found to be diffusely swollen on physical examination, and a monoclonal antibody assay of lymphocyte subpopulations performed within two months of this examination showed his T-helper cell count to be 1,128/cc. The ratio of the T-helper to T-suppressor cells was found to be 1.67, which was within the range of normal. Lymph node size gradually increased. A second assay of lymphocyte subpopulations performed a little more than three months later showed that the $T_4/T_8$ ratio was now 1.78, with T-helpers at 698/cc and T-suppressors at 393/cc.

A third assay performed nearly six months later showed a reversal of the normal $T_4/T_8$ ratio at 0.93. T-helper cells were 1,020/cc and T-suppressor cells were 1,091/cc.

Symptomatic AIDS continued, and a fourth assay performed two and a half months later indicated continued reversal of the normal $T_4/T_8$ ratio, at 0.91. T-helper cells were 605/cc and T-suppressors were 662/cc. The patient had become increasingly fatigued with generalized weakness.

The thiophosphoric acid triaziridide derivative of the alkaloid extracts of Chelidonium majus L. in the form of the hydrochloride salt, tradename "Ukrain", was administered in aqueous solution on each of three days intravenously. Each dose was 10 mg. Thereafter intramuscular injections of 5 mg. each were administered twice a day (B.I.D.) to total dose of 150 mg.

At the fifth monoclonal antibody examination of lymphocyte subpopulations from this patient, a little more than two months later, the ratio of T-helper to T-suppressor cells exhibited an unexpected reversal from the 0.91 level of the preceding assay to 20.5, higher than this patient had ever had during the course of his HIV infection. The level of T-helper cells had increased from 605/cc to 1,133/cc and the T-suppressor cells had decreased from 662/cc to 552/cc.

Simultaneously, the patient experienced relief from his fatigue and weakness. On physical examination, diminution of lymph node enlargement from that noted in previous examinations could be detected.

The results of these five assays are given below in tabular form:

|  | I | II | III | IV | V |
|---|---|---|---|---|---|
| LEUCOCYTE/CC. | 4400 | 3900 | 5500 | 4400 | 5100 |
| LYMPHOCYTES/CC. | 2508 (57%) | 2186 (56%) | 3520 (64%) | 1892 (43%) | 2907 (57%) |
| $T_4$ HELPER CELLS/CC. | 1128 (45%) | 698 (32%) | 1020 (29%) | 605 (32%) | 1133 (39%) |
| $T_8$ SUPPRESSOR CELLS/CC. | 677 (27%) | 393 (18%) | 1091 (31%) | 662 (35%) | 552 (19%) |
| RATIO $T_4/T_8$ | 1.67 | 1.78 | 0.93 | 0.91 | 2.05 |

The results shown in this example demonstrate the objective and subjective improvement in the condition of a patient with AIDS upon treatment according to the method of this invention.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

I claim:

1. A method of treating a human patient infected with an infectious agent which comprises the ability to mount an effective immunological response, said method comprising administering to the patient a therapeutically effective amount of a mixture of non-toxic cytostatic alkaloid derivatives wherein at least a portion of said mixture is comprised of derivatives of extracts of *Chelidonium majus L.*

2. A method as recited in claim 1 wherein said patient is infected with the Human Immunodeficiency Virus.

3. A method as recited in claim 1 wherein said infectious agent results in the patient having AIDS-Related Complex.

4. A method as recited in claim 1 wherein said infectious agent results in the patient having AIDS.

5. A method as recited in claim 1 wherein said infectious agent results in an introduced opportunistic infection in a patient suffering from AIDS.

6. A method as recited in claim 1 wherein said mixture of non-toxic cytostatic alkaloid derivatives comprises alkaloid-thiophosphate derivatives.

7. A method as recited in claim 6 wherein said mixture of non-toxic cytostatic alkaloid derivatives comprises thiophosphoric acid triaziridide derivatives.

8. A method as recited in claim 7 wherein said thiophosphoric acid triaziridide derivatives are derivatives of alkaloid extracts of *Chelidonium majus L.*

9. A method as recited in claim 8 wherein said thiophosphoric acid triaziridide derivatives of alkaloid extracts of *Chelidonium majus L.* are administered in aqueous solution in the form of a water soluble pharmaceutically acceptable salt.

10. A method as recited in claim 9 wherein said thiophosporic acid triaziridide derivatives of alkaloid comprise chelilutine thiophosphoric acid triaziridid hydrochloride.

11. A method as recited in claim 9 wherein said salt is the hydrochloride salt.

12. A method as recited in any one of claims 1–5, 6 and 7–12 wherein said mixture of non-toxic cytostatic alkaloid derivatives is administered in an amount sufficient to reverse T-helper cell deficiency and diminish the overgrowth of T-suppressor cells in said patient.

* * * * *